US00PP36764P2

(12) United States Plant Patent
Danziger

(10) Patent No.: US PP36,764 P2
(45) Date of Patent: Jun. 24, 2025

(54) ***BIDENS* PLANT NAMED 'DPWBIDCAPR'**

(50) Latin Name: *Bidens ferulifolia*
Varietal Denomination: DPWBIDCAPR

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 18/956,252

(22) Filed: Nov. 22, 2024

(51) Int. Cl.
*A01H 5/02* (2018.01)
*A01H 6/14* (2018.01)

(52) U.S. Cl.
USPC ..... Plt./410

(58) Field of Classification Search
USPC ..... Plt./263.1, 410
See application file for complete search history.

(56) References Cited

U.S. PATENT DOCUMENTS

PP34,511 P2 * 8/2022 Nishikawa ..... Plt./410

* cited by examiner

*Primary Examiner* — Karen M Redden
(74) *Attorney, Agent, or Firm* — C. Anne Whealy

(57) ABSTRACT

A new and distinct cultivar of *Bidens* plant named 'DPWBIDCAPR', characterized by its upright to outwardly spreading and uniformly mounding to semi-trailing plant habit; moderately vigorous to vigorous growth habit; freely branching habit; dense and bushy plant form; freely flowering habit; long flowering period; single-type inflorescences; inflorescences with solid dark red-colored ray florets that with subsequent development become dark reddish orange (distally) and yellow (proximally) bi-colored; and good garden performance.

2 Drawing Sheets

Figure 1:
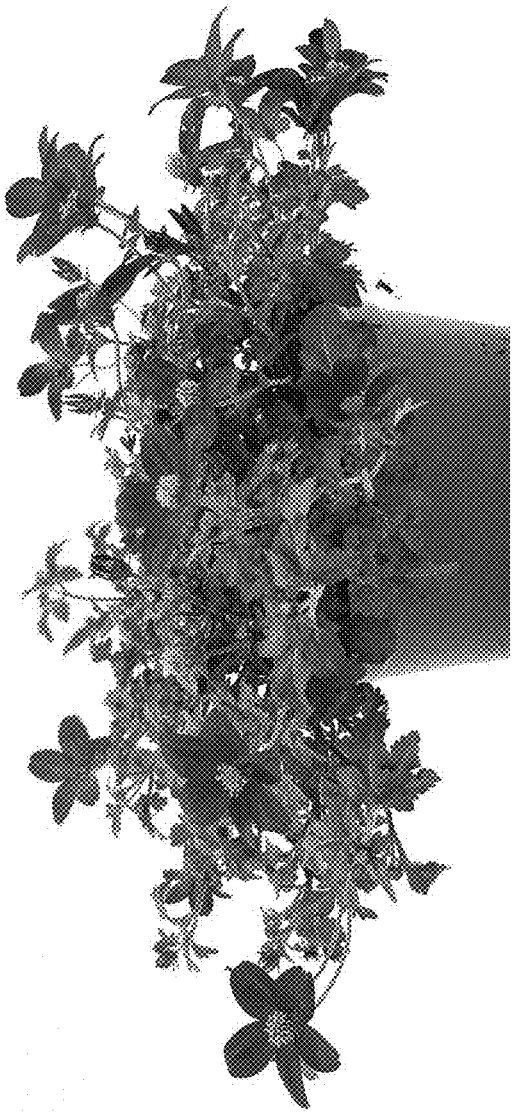

Botanical designation: *Bidens ferulifolia.*
Cultivar denomination: 'DPWBIDCAPR'.

BACKGROUND OF THE INVENTION

The present invention relates to a new and distinct cultivar of *Bidens* plant, botanically known as *Bidens ferulifolia* and hereinafter referred to by the name 'DPWBIDCAPR'.

The new *Bidens* plant is a product of a planned breeding program conducted by the Inventor in Moshav Mishmar Hashiva, Israel. The objective of the breeding program is to create new uniformly mounding *Bidens* plants with unique ray floret coloration.

The new *Bidens* plant originated from an open-pollination in Moshav Mishmar Hashiva, Israel in 2017 of a proprietary selection of *Bidens ferulifolia* identified as code number BD-17-3097, not patented, as the female, or seed, parent with an unknown selection of *Bidens ferulifolia* as the male, or pollen, parent. The new *Bidens* plant was discovered and selected by the Inventor as a single flowering plant from within the progeny of the stated open-pollination in a controlled greenhouse environment in Moshav Mishmar Hashiva, Israel in 2018.

Asexual reproduction of the new *Bidens* plant by vegetative terminal cuttings in a controlled environment in Moshav Mishmar Hashiva, Israel since 2018 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'DPWBIDCAPR'. These characteristics in combination distinguish 'DPWBIDCAPR' as a new and distinct *Bidens* plant:

1. Upright to outwardly spreading and uniformly mounding to semi-trailing plant habit.
2. Moderately vigorous to vigorous growth habit.
3. Freely branching habit; dense and bushy plant form.
4. Freely flowering habit.
5. Long flowering period.
6. Single-type (daisy) inflorescences.
7. Inflorescences with solid dark red-colored ray florets that with subsequent development become dark reddish orange (distally) and yellow (proximally) bi-colored.
8. Good garden performance.

Plants of the new *Bidens* differ primarily from plants of the female parent selection in ray floret color as plants of the new *Bidens* have ray florets that are solid dark red in color and with subsequent development becoming dark reddish orange (distally) and yellow (proximally) bi-colored whereas ray florets of plants of the female parent selection are red in color surrounded with yellow-colored margins.

Plants of the new *Bidens* can be compared to plants of *Bidens ferulifolia* 'DBIDBLZSAR', not patented. In side-by-side comparisons, plants of the new *Bidens* differ primarily from plants of 'DBIDBLZSAR' in the following characteristics:

1. Plants of the new *Bidens* are more outwardly spreading and mounding than and not as upright as plants of 'DBIDBLZSAR'.
2. Ray florets of plants of the new *Bidens* are solid dark red in color and with subsequent development becoming dark reddish orange (distally) and yellow (proximally) bi-colored whereas plants of 'DBIDBLZSAR' are red in color surrounded with yellow-colored margins.

BRIEF DESCRIPTION OF THE PHOTOGRAPHS

The accompanying colored photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph on the first sheet (FIG. 1) is a side perspective view of a typical flowering plant of 'DPWBID-CAPR' grown in a container.

Figure 2:
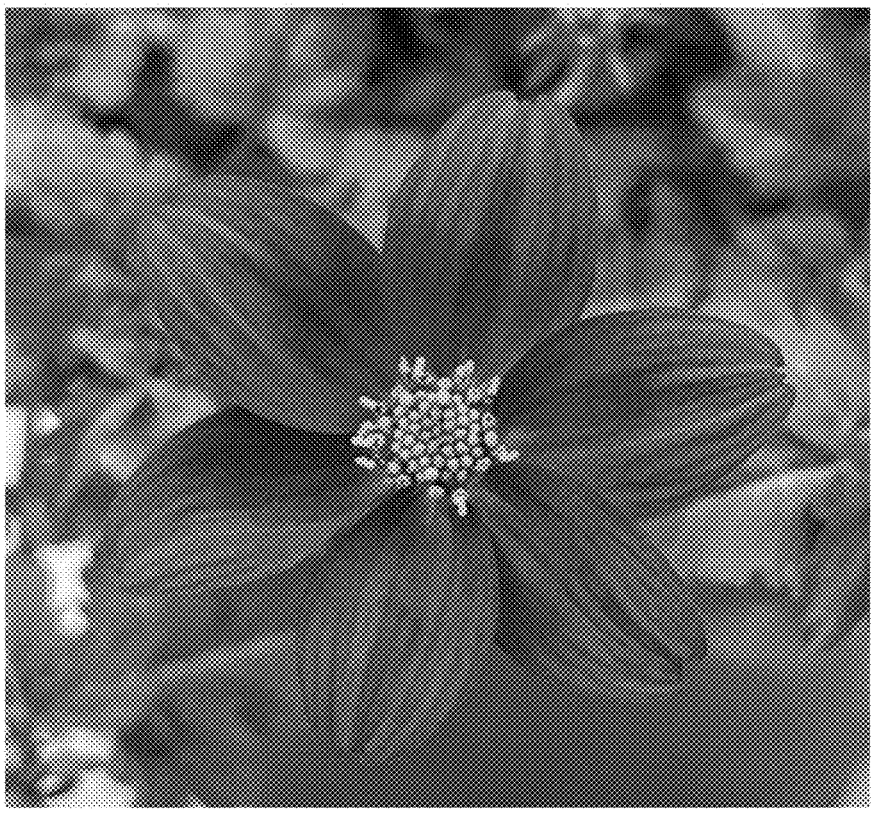

The photograph on the second sheet (FIG. 2) is a close-up view of a typical developing inflorescence of 'DPWBID-CAPR'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial *Bidens* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Bidens ferulifolia* 'DPWBID-CAPR'.

Parentage:

*Female, or seed, parent*.—Proprietary selection of *Bidens ferulifolia* identified as code number BD-17-3097, not patented.

*Male, or pollen, parent*.—Unknown selection of *Bidens ferulifolia*, not patented.

Propagation:

*Type*.—By vegetative terminal cuttings.

*Time to initiate roots, summer*.—About four to seven days at temperatures ranging from 25° C. to 30°.

*Time to initiate roots, winter*.—About six to ten days at temperatures ranging from 10° C. to 25°.

*Time to produce a rooted young plant, summer*.—About 12 to 18days at temperatures ranging from 25° C. to 30°.

*Time to produce a rooted young plant, winter*.—About 15 to 21 days at temperatures ranging from 10° C. to 25°.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to outwardly spreading and uniformly mounding to semi-trailing plant habit; moderately vigorous to vigorous growth habit and moderate to rapid growth rate.

*Branching habit*.—Freely branching habit typically with about eight to ten primary lateral branches each with secondary lateral branches potentially developing at every node; dense and bushy appearance.

*Plant height*.—About 14 cm to 16 cm.

*Plant diameter or spread*.—About 36 cm to 42 cm.

*Lateral branches*.—Length, primary branches: About 18 cm to 23 cm. Diameter, primary branches: About 2.5 mm. Internode length: About 3.1 cm to 3.5 cm. Strength: Strong, flexible; wiry. Aspect: Upright to outwardly to semi-trailing and decumbent. Texture and luster: Densely pubescent; matte. Color, developing: Close to 146A and slightly and variably tinged with close to N77A. Color, developed: Close to 146A strongly tinged with close to N77A.

Leaf description:

*Arrangement*.—Opposite, simple.

*Length*.—About 3.2 cm to 3.5 cm.

*Width*.—About 3.1 cm to 3.4 cm.

*Shape*.—Roughly deltoid, pinnatisect; tri-lobed.

*Apex*.—Acute with cuspidate tip.

*Base*.—Truncate.

*Margin*.—Serrate; indentations are shallow and divergent.

*Texture and luster, upper and lower surfaces*.—Smooth, glabrous; matte.

*Venation pattern*.—Pinnate, reticulate.

*Color*.—Developing leaves, upper surface: Close to NN137A. Developing leaves, lower surface: Close to 138A to 138B. Fully expanded leaves, upper surface: Close to NN137A; venation, close to 146A. Fully expanded leaves, lower surface: Close to 138A to 138B; venation, close to 146A to 146B.

*Petioles*.—Length: About 1.3 cm to 1.5 cm. Diameter: About 2 mm to 3 mm. Strength: Moderately strong, flexible. Texture and luster, upper and lower surfaces: Moderately pubescent; matte. Color, upper and lower surfaces: Close to 144A.

Inflorescence description:

*Appearance*.—Single type (daisy) solitary inflorescences developing on terminal and axillary peduncles; inflorescence form with ray and disc florets; inflorescences positioned above the foliar plane on strong peduncles; inflorescences face mostly upright.

*Flowering habit*.—Freely flowering habit with more than 1,000 inflorescences and inflorescence buds developing during the flowering season.

*Fragrance*.—None detected.

*Flowering response*.—Early flowering habit, plants begin flowering about five to seven weeks after planting rooted young plants.

*Natural flowering season*.—Long flowering period, plants flower continuously from spring until frost in temperate regions and year-round in milder (above freezing temperatures) climates.

*Inflorescence longevity*.—Depending on temperatures, inflorescences last about seven to ten days on the plant; inflorescences persistent.

*Inflorescence buds*.—Height: About 4.5 mm. Diameter: About 4.5 mm. Shape: Spherical. Texture and luster: Smooth, glabrous; matte. Color: Close to 148A.

*Inflorescence size*.—Diameter: About 3 cm to 3.25 cm. Height: About 1 cm. Disc diameter: About 6 mm.

*Receptacles*.—Receptacle diameter: About 4 mm. Receptacle height: About 4 mm. Receptacle shape: Domed. Receptacle color: Close to between 144A and 146A.

*Ray florets*.—Number of ray florets per inflorescence: About five to six arranged in a single whorl. Length: About 1.6 cm. Width: About 8 mm. Shape: Oblanceolate. Apex: Shallowly praemorse. Base: Obtuse and fused at the base into a short tube. Margin: Entire; not undulate. Aspect: Mostly horizontal, apices slightly reflexing with development; slightly concave. Texture and luster, upper and lower surfaces: Longitudinally ribbed, glabrous; matte. Color: When opening, upper surface: Close to 53A. When opening, lower surface: Close to 46A. Fully opened, upper surface: Close to N34A; at the base, close to 12A; venation, similar to lamina; with subsequent development, distally, becoming closer to 169A variably tinged with close to N34A and proximally, closer to 17A to 17B. Fully opened, lower surface: Close to N34A to N34B; venation, similar to lamina colors; with development subsequent, distally, becoming closer to 169B to 169C and proximally, closer to 14A.

*Disc florets*.—Number of disc florets per inflorescence: About 50 in about four to five whorls at the center of the receptacle. Length: About 7.5 mm to 8 mm. Diameter: About 1 mm. Shape: Tubular, slender; apex, five-pointed. Texture and luster: Smooth, glabrous; slightly glossy. Color, inner and outer surfaces: Close to 6A and at the base, close to 154D.

*Phyllaries*.—Quantity per inflorescence: About eight to twelve arranged in a single whorl. Length: About 3 mm. Width: About 1 mm. Shape: Linear. Apex: Acute. Base: Truncate. Margin: Entire. Texture and luster, upper and lower surfaces: Slightly pubescent; matte. Color, upper and lower surfaces: Close to between 139A and 147A.

*Peduncles*.—Length, terminal peduncle: About 4.5 cm to 5 cm. Length, second peduncle: About 3.5 cm to 4.2 cm. Diameter: About 1 mm. Strength: Strong; flexible; wiry. Aspect: Terminal peduncles, mostly erect; axillary peduncles, about 30° to 45° from vertical. Texture and luster: Densely pubescent; matte. Color: Close to 144A.

*Reproductive organs*.—Androecium: Present on disc florets only. Quantity per disc floret: Five. Filament length: About 4 mm. Filament color: Close to 144D. Anther length: About 1 mm. Anther shape: Oblong. Anther color: Close to 13A. Pollen amount: None observed. Gynoecium: Present on disc florets only. Quantity per floret: One. Pistil length: About 4.5 mm. Style length: About 3.5 mm. Style color: Close to 154D. Stigma diameter: Less than 1 mm. Stigma shape: Bi-parted. Stigma color: Close to 12A. Ovary color: Close to 144A to 144B.

*Seeds and fruits*.—To date, seed and fruit development have not been observed on plants of the new *Bidens*.

Pathogen & pest resistance: To date, plants of the new *Bidens* have not been shown to be resistant to pathogens and pests common to *Bidens* plants.

Garden performance: Plants of the new *Bidens* have been observed to have good garden performance and to tolerate temperatures from about 2° C. to about 40° C. and are suitable for USDA Hardiness Zones 9 and 11.

It is claimed:

1. A new and distinct *Bidens* plant named 'DPWBIDCAPR' as herein illustrated and described.

* * * * *